ue010143642B2

(12) United States Patent
Chavan et al.

(10) Patent No.: US 10,143,642 B2
(45) Date of Patent: Dec. 4, 2018

(54) SUNSCREEN MOLECULE AND COMPOSITIONS THEREOF

(71) Applicant: Conopco, Inc., Englewood Cliffs, NJ (US)

(72) Inventors: Mohan Vijaykumar Chavan, Mumbai (IN); Vijay Ramchandra Gadgil, Bangalore (IN); Balu Kunjupillai, Ngapattinam (IN); Ashish Anant Vaidya, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 347 days.

(21) Appl. No.: 15/104,329

(22) PCT Filed: Dec. 11, 2014

(86) PCT No.: PCT/EP2014/077324
§ 371 (c)(1),
(2) Date: Jun. 14, 2016

(87) PCT Pub. No.: WO2015/101468
PCT Pub. Date: Jul. 9, 2015

(65) Prior Publication Data
US 2016/0310398 A1 Oct. 27, 2016

(30) Foreign Application Priority Data
Dec. 30, 2013 (EP) ..................................... 13199776

(51) Int. Cl.
*A61K 8/63* (2006.01)
*A61Q 17/04* (2006.01)
*C07J 41/00* (2006.01)
*C07J 9/00* (2006.01)

(52) U.S. Cl.
CPC ............... *A61K 8/63* (2013.01); *A61Q 17/04* (2013.01); *C07J 9/005* (2013.01); *C07J 41/0094* (2013.01); *A61K 2800/57* (2013.01)

(58) Field of Classification Search
None
See application file for complete search history.

(56) References Cited

U.S. PATENT DOCUMENTS 4,999,186 A 3/1991 Sabatelli et al.

FOREIGN PATENT DOCUMENTS

| EP | 0416837 | 3/1991 |
| JP | S63135324 | 6/1988 |
| WO | WO9414410 | 7/1994 |
| WO | WO2013123658 | 8/2013 |

OTHER PUBLICATIONS

Search Report & Written Opinion in PCTEP2014077324, dated Feb. 17, 2015.
Search Report and Written Opinion in EP13199776, dated Jun. 4, 2014.

*Primary Examiner* — Nicole P Babson
(74) *Attorney, Agent, or Firm* — Greenberg Traurig, LLP

(57) ABSTRACT

The present invention relates to a broad spectrum stable sunscreen molecule having the general structure (Formula) where "X" is an organic sunscreen belonging to the UVA class and "Y" is an organic sunscreen belonging to UVB class or vice-versa. The invention also relates to a stable sunscreen composition comprising the inventive sunscreen molecule, a UV-B organic sunscreen and a cosmetically acceptable base. The invention also relates to a method of providing UV protection to the sun-exposed parts of human or animal body comprising the step of applying the above composition.

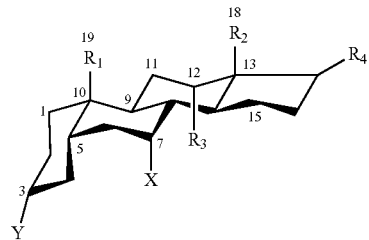

8 Claims, No Drawings

SUNSCREEN MOLECULE AND COMPOSITIONS THEREOF

FIELD OF THE INVENTION

The present invention relates to a novel sunscreen molecule which is broad spectrum and stable. The invention also relates to a sunscreen composition and method of providing UV protection comprising the same.

BACKGROUND OF THE INVENTION

Solar radiation includes ultraviolet (UV) radiation wavelength of which is between 200 nm and 400 nm. Exposure of skin to UV-A (320 to 400 nm) and UV-B (290 to 320 nm) radiation causes various problems like reddening of the skin, localized irritation, sunburn, melanoma and formation of wrinkles. UV radiation is also known to cause damage to hair. Therefore, it is desirable to protect the skin and other keratinous substrates of the human body from the harmful effects of both UV-A and UV-B radiation.

Cosmetic compositions comprising sunscreen agents are used to protect the skin against UV radiation. Sunscreen agents are generally classified as organic sunscreens and inorganic sunscreens.

Inorganic sunscreens are generally inorganic particles which provide protection to the skin by way of blocking the solar radiation. Examples of such sunscreens are zinc oxide and titanium dioxide. Problem with using inorganic sunscreens is that they cannot be used at high concentrations since they give an unnatural whiteness to the skin on which they are applied.

Organic sunscreens are organic compounds which act by absorbing the solar radiation at a particular range of wavelength and emitting them at a different wavelength. Organic sunscreens are classified into UV-A sunscreens and UV-B sunscreens, depending on the wavelength range over which they offer protection. The most commonly used UV-A sunscreen is of the dibenzoylmethane class. UV-B organic sunscreens from the class of cinnamic acid, salicylic acid, and diphenyl acrylic acid are well known and used in sunscreen compositions. In order to have sunscreen protection over a wide range of wavelengths, sunscreen compositions generally include both a UV-A sunscreen and a UV-B sunscreen. Problem with including both a UV-A sunscreen and a UV-B sunscreen is that firstly including both of these makes the composition expensive. UV-A sunscreens are sometimes not very stable in use, especially in the presence of UV-B sunscreens. Further they cannot be included in high concentrations since they have inherent safety and stability issues when used at these high levels.

In order to overcome this, sunscreen molecules where both UV-A and/or UV-B sunscreens have been attached to a silicone backbone to get broad spectrum protection have been reported.

U.S. Pat. No. 4,999,186A (P&G, 1987) relates to novel sunscreen agent which has the ability to absorb both UVA and UVB wavelength radiation and to compositions and methods of providing sunscreen benefits using these agents. The sunscreen agents comprise a specific type of UVA-absorbing chromophore covalently bonded to a specific type of UVB-absorbing chromophore.

JP63135324A (Nisshin Oil Mills, 1996) discloses a cinnamic acid ester compound of cholesterol as an active ingredient, having antiinflammatory action effective to sunlight dermatitis and especially having much effect for inhibiting and preventing erythema and inflammation by light of ultraviolet area in sunlight rays.

It is thus an object of the present invention to provide for a sunscreen molecule that exhibits protection against a wide range of ultraviolet radiation wavelength.

It is another object of the present invention to provide for a broad spectrum sunscreen molecule that is stable for many hours after exposure to sunlight.

By way of the present invention, a UV-A sunscreen and a UV-B sunscreen are attached to a bile acid (e.g. cholic acid) backbone which exhibits very broad spectrum UV-sunscreen efficacy while being more stable than known heretofore. The present invention is an improvement over the known art since better sun screening efficacy is obtained while having higher stability over time.

SUMMARY OF THE INVENTION

The first aspect of the present invention provides for a broad spectrum stable sunscreen molecule having the structure

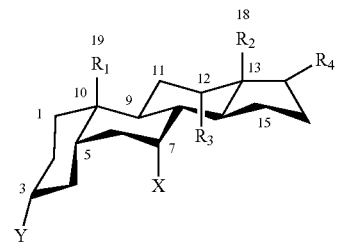

where,
R1 and R2 are selected from C1 to C20 linear or branched alkyl, C3-C10 cycloalkyl, polycycloalkyl, heterocyclic, aryl, alkoxy, alkenyl or alkynyl groups,
R3 is —H or —OH or R1
R4 is selected from C1 to C20 linear or branched alkyl, C3-C10 cycloalkyl, polycycloalkyl, heterocyclic, aryl, alkoxy, alkenyl or alkynyl groups containing carboxylic acid group in free form or its ester derivative;
Or
R4 is H or is selected from C1 to C20 linear or branched alkyl, C3-C10 cycloalkyl, polycycloalkyl, heterocyclic, aryl, alkoxy, alkenyl or alkynyl groups containing carboxylic acid; wherein acid group is attached to the polymer through ester linkage
Or
R4 is same as R1 or R2
Or
R4 is an "organoheteryl group" or polymer backbone or cross-polymer backbone or rigid organic or inorganic support covalently attached through the "hetero atom"
"X" is an organic sunscreen belonging to the UVA class and "Y" is an organic sunscreen belonging to UVB class or vice-versa.

The second aspect of the present invention provides for a stable sunscreen composition comprising (i) a sunscreen molecule of the first aspect (ii) a UV-B organic sunscreen belonging to the cinnamic acid, salicylate, diphenyl acrylate derivatives, triazine, triazole, and imidazole compounds group; and (iii) a cosmetically acceptable base.

According to yet another aspect of the present invention there is provided a method of providing UV protection to the sun-exposed parts of human or animal body comprising the step of applying a composition of the present invention on to the desired part.

DETAILED DESCRIPTION OF THE INVENTION

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description and claims indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

By "Sunscreen Composition" as used herein, is meant to include a composition for topical application to sun-exposed areas of the skin and/or hair of mammals, especially humans. Such a composition may be generally classified as leave-on or rinse off, and includes any product applied to a human body for also improving appearance, cleansing, odor control or general aesthetics. It is more preferably a leave-on product. The composition of the present invention can be in the form of a liquid, lotion, cream, foam, scrub, gel, or toner, or applied with an implement or via a face mask, pad or patch. Non-limiting examples of such sunscreen compositions include leave-on skin lotions, creams, antiperspirants, deodorants, lipsticks, foundations, mascara, sunless tanners and sunscreen lotions. "Skin" as used herein is meant to include skin on the face and body (e.g., neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

An advantage of the present invention is that use of the novel sunscreen molecule of the invention ensures that only one sunscreen need be used instead of two sunscreens (a UVA and a UVB sunscreen) that are generally used. Further the use of this novel molecule ensures high uniform protection over time of use in the UV-A region which is generally not achieved through use of conventional UV-A sunscreens especially in the presence of UV-B sunscreen. The photostable sunscreen molecule of the invention comprises a UV-A sunscreen moiety and a UV-B sunscreen moiety attached to a bile acid (e.g. cholic acid) based backbone.

The novel sunscreen of the invention has the structure:

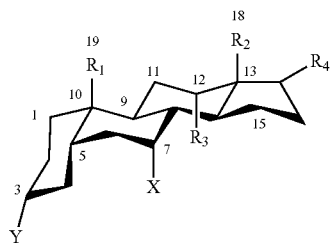

Where R1, R2, R3 and R4 are groups as defined hereinabove.

"X" is an organic sunscreen belonging to the UVA class and "Y" is an organic sunscreen belonging to UVB class or vice-versa. In other words, X could be an organic sunscreen belonging to the UVA class or an organic sunscreen belonging to the UVB class. Similarly Y could be an organic sunscreen belonging to the UVA class or an organic sunscreen belonging to the UVB class. But in a given molecule of the invention both X and Y do not belong to the same class of organic UV sunscreens.

According to a preferred aspect of the present invention, in the sunscreen molecule of the present invention R1, R2, R3 are each a methyl group and R4 is 4-pentanoic acid methyl ester. Preferably, when the pendent group X or Y is an organic UVA sunscreen, the UVA organic sunscreen is a dibenzoyl methane, a benzophenone, or a triazine compound. Similarly, in a preferred aspect, when the pendent group X or Y is an organic UVB sunscreen, the UVB organic sunscreen is a cinnamate, salicylate, diphenyl acrylate derivatives, triazine, triazole, and imidazole compound. Further more preferably the organic UVA sunscreen referred above is a dibenzoylmethane compound and the organic UVB sunscreen is a dipenyl acrylate compound.

The dibenzoylmethane compound is preferably 4-tert-butyl-4'-methoxydibenzoylmethane, 2-methyldibenzoylmethane, 4-methyl-dibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert.-butyl-4'-methoxydibenzoylmethane.

The most preferred UVB sunscreen appended to the sunscreen molecule of the present invention is a diphenyl acrylate compound. Most preferred diphenyl acrylate compound is 2-ethylhexyl 2-cyano-3,3-diphenyl-2-propenoate which is sold under the brand name of Octocrylene™.

Most preferably, in the novel sunscreen molecule of the present invention, X is a dibenzoyl methane compound and Y is a dipenyl acrylate compound.

According to an especially preferred aspect of the present invention the sunscreen molecule has the structure

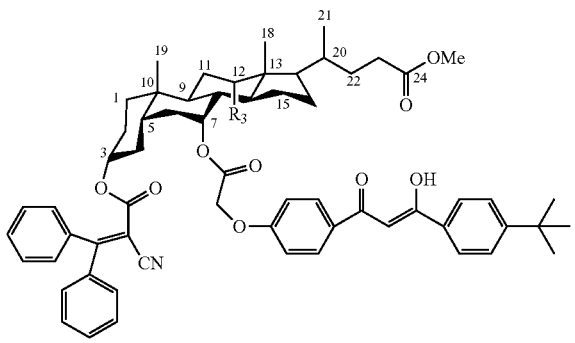

R3 is H or OH

A preferred aspect of the present invention provides for the above compound to be prepared by a process comprising the following general steps:

Step 1: Esterification of Bile Acid (e.g. Chenodeoxycholic Acid):

Bile acid having hydroxyl group is reacted with methanol in the presence of Lewis acid preferably concentrated sulphuric acid at room temperature to give methyl ester of corresponding Bile acid Step 2: Synthesis of UVB Sunscreen Acid Ester of UVB absorbing molecule (e.g. 2-ethylhexyl 2-cyano-3,3-diphenyl-2-propenoate) is hydrolysed with strong base in hydroalcoholic medium at room temperature to give corresponding acid Step 3: Covalent Attachment of UVB Sunscreen Acid (at C-3 Position) to Methyl Ester of Bile Acid Product from step 1 is esterfied with product from step 2 with esterification agent preferably Dicyclohexyl carbodimide and aromatic nitrogen containing base preferably N,N-dimethylamino pyridine in chlorinated solvent under inert atmosphere and at room temperature.

Step 4: Derivatization of UVB Attached Methyl Ester of Bile Acid at C-7 Position Product from step 3 is esterfied with halo acetyl halides in the presence of metal hydrides and quaternary ammonium halides under the inert atmosphere to give C7-derivatised UVB attached bile acid methyl ester Step 5: Synthesis of UVA Chromophore (e.g. Dibenzoylmethane)

Acetophenone derivative containing at least one phenolic hydroxyl group is reacted with Alkyl benozoate in the presence of metal hydrides in alkyl ether of dihydroxy alkane at 100-120° C. to give the corresponding dibenzoylmethane derivative.

Step 6: Covalent Attachment of UVA Chromophore at C-7 Derivatized Methyl Ester of UVB Attached Bile Acid Product from step 5 is alkylated with product from step 4 in the presence of metal carbonate in aliphatic ketone at its boiling point under inert atmosphere to give broad spectrum photostable sunscreen molecule.

According to another aspect of the present invention, there is provided a stable sunscreen composition comprising (i) a sunscreen molecule of the invention (ii) a UV-B organic sunscreen belonging to the cinnamic acid group, salicylate, diphenyl acrylate derivatives, triazine, triazole, and imidazole compounds; and (iii) a cosmetically acceptable base.

In the composition of the invention the sunscreen molecule of the invention is preferably present in 1 to 15%, preferably 4 to 10% by weight of the composition. The organic UV-B organic sunscreen included in the sunscreen composition of the invention preferably belongs to the cinnamic acid compound group. It is preferably 2-ethylhexyl-4-methoxy cinnamate which is commercially available as Parsol MCX. The UVB organic sunscreen compound included in the composition is preferably included in 0.1 to 10%, more preferably 0.7 to 7% by weight of the composition; further most preferred is 2.4 to 5%.

The composition of the invention comprises a cosmetically acceptable base. The cosmetically acceptable base preferably comprises a fatty acid or a silicone compound. When the cosmetically acceptable base comprises fatty acid it is preferably present in 1 to 25% by weight of the composition. When the cosmetically acceptable bases are such as to have a product in a cream, lotion, or emulsion format, it generally comprises fatty acid. Of these formats, a more preferred format is a cream or lotion, further more preferably a cream. Vanishing cream base is one which comprises 3 to 25%, more preferably 5 to 20% fatty acid, which is a preferred format of the composition of the invention. In this, the base preferably comprises 0.1 to 10%, more preferably 0.1 to 3% soap. $C_{12}$ to $C_{20}$ fatty acids are especially preferred in vanishing cream bases, further more preferred being $C_{14}$ to $C_{18}$ fatty acids. In creams, the fatty acid is preferably substantially a mixture of stearic acid and palmitic acid. Soaps in the vanishing cream base include alkali metal salt of fatty acids, like sodium or potassium salts The soap is preferably the potassium salt of the fatty acid mixture. The fatty acid in vanishing cream base is often prepared using hystric acid which is substantially (generally about 90 to 95%) a mixture of stearic acid and palmitic acid. Thus, inclusion of hystric acid and its soap to prepare the vanishing cream base is within the scope of the present invention. It is particularly preferred that the composition comprises at least 6%, preferably at least 10%, more preferably at least 12% fatty acid. The cosmetically acceptable base is usually from 10 to 99.9%, preferably from 50 to 99% by weight of the composition. Another preferred base is a lotion. Lotions generally comprise 1 to 20% fatty acid. The cosmetically acceptable base preferably includes water. Water is preferably included in 35 to 90%, more preferably 50 to 85%, further more preferably 50 to 80% by weight of the composition.

An especially suitable cosmetically acceptable base is one which comprises a water-in-oil emulsion comprising silicone oils as the continuous phase. The water in oil emulsions preferably comprise a crosslinked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. The creation of cross-linkages between linear polymers, such as dimethicone, converts the linear polymer into a silicone elastomer. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions.

Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer]; EL-8050 [INCI Name: Isododecane (and) Dimethicone/Bis-Isobutyl PPG 20 Crosspolymer] DC 9040, DC9041, DC9045 (Dimethicone crosspolymer); DC 9506, 9509 (Dimethicone vinyl dimethicone crosspolymer); Shin-Etsu KSG-15, KSG-16, KSG-17 (Dimethicone vinyl dimethicone crosspolymer). It is further preferred that the composition comprises 5 to 95% silicone elastomer by weight of the composition.

Other useful sun-protective agents e.g. inorganic sunblocks may be preferably used in the present invention. These include, for example, zinc oxide, iron oxide, silica, such as fumed silica, or titanium dioxide. The total amount of sun block that is preferably incorporated in the composition according to the invention is from 0.1 to 5% by weight of the composition.

The composition of the invention may additionally comprise a skin lightening agent. The skin lightening agent is preferably chosen from a vitamin B3 compound or its derivative e.g. niacin, nicotinic acid, niacinamide or other well known skin lightening agents e.g. aloe extract, ammonium lactate, azelaic acid, kojic acid, citrate esters, ellagic acid, glycolic acid, green tea extract, hydroquinone, lemon extract, linoleic acid, magnesium ascorbyl phosphate, vitamins like vitamin B6, vitamin B12, vitamin C, vitamin A, a dicarboxylic acid, resorcinol derivatives, hydroxycarboxylic acid like lactic acid and their salts e.g. sodium lactate, and mixtures thereof. Vitamin B3 compound or its derivative e.g. niacin, nicotinic acid, niacinamide are the more preferred skin lightening agent as per the invention, most preferred being niacinamide. Niacinamide, when used, is preferably present in an amount in the range of 0.1 to 10%, more preferably 0.2 to 5% by weight of the composition.

The composition according to the invention may also comprise other diluents. The diluents act as a dispersant or carrier for other materials present in the composition, so as to facilitate their distribution when the composition is applied to the skin. Diluents other than water can include liquid or solid emollients, solvents, humectants, thickeners and powders.

The composition of the invention may comprise a conventional deodourant base as the cosmetically acceptable carrier. By a deodorant is meant a product in the stick, roll-on, or propellant medium which is used for personal deodorant benefit e.g. application in the under-arm or any other area which may or may not contain anti-perspirant actives.

Deodorant compositions can generally be in the form of firm solids, soft solids, gels, creams, and liquids and are dispensed using applicators appropriate to the physical characteristics of the composition.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

Another aspect of the present invention relates to a method of providing UV protection to the sun-exposed parts of human or animal body comprising the step of applying a composition of the invention on to the desired part.

The invention is now further described by way of the following non-limiting examples.

EXAMPLES

Examples 1 to 6: Stability of Sunscreen Active of the Invention as Compared to Other Sunscreens and Combinations Sunscreen actives singly or as combinations as shown in Table-1 were checked for stability using the following procedure:

The method was based on spotting the HPTLC plates (in duplicate) with the sunscreen molecules of interest along with potential quencher molecules or formulations. The plate is then exposed to UV radiation (intensity 5.5 mW/cm$^2$) for 120 minutes. Following this the chromatographic separation was carried out using appropriate solvent system. Densitometry analysis is done to determine the amount of sunscreen degraded. Stock solutions were prepared in methanol following the ratios as mentioned in the following table. 14 μL of stock solutions were loaded (3 mm width; 16 mm separation) on a 10×10 cm F254 HPTLC plate, using CAMAG LINOMAT 5 applicator equipped with a 100 μL micro-syringe (Hamilton, Switzerland). Ascending chromatography was performed at a distance of 85 mm in a TLC chamber using n-hexane-ethyl acetate 9:1 (v/v) as the mobile phase (~10 mL). The plates were dried at room temperature and subjected to ultraviolet absorption densitometry scan. The concentration dependent fluorescent bands due to presence of sunscreens were detected with a linear scan at 357 nm, using Camag TLC Scanner 3, in the presence of deuterium source. Slit width of 8×0.4 mm and scanning rate of 20 mm s$^{-1}$ were maintained during each densitometry scan. Concentrations of Parsol 1789 & the compound of present invention on each lane were determined from densitogram peak areas; prior and after the sun exposure using Win CATS Planar chromatography manager software.

Results are presented in the following table:

TABLE 1

| Example | Composition/ active (wt %) | % active, 0 hr | % active, 1 hr | % active, 2 hr |
|---|---|---|---|---|
| 1 | Parsol 1789 (1%) | 100 | 28 | 5 |
| 2 | Parsol 1789 (1%) + Parsol MCX (2.5%) | 100 | 11 | 2 |
| 3 | Parsol 1789 (1%) + Octocrylene (1%) | 100 | 89 | 72 |
| 4 | Parsol 1789 (1%) + Parsol MCX (2.5%) + Octocrylene (1%) | 100 | 70 | 43 |
| 5 | Compound of present invention (3.14%) | 100 | 93 | 86 |
| 6 | Compound of present invention (3.14%) + Parsol MCX (2.5%) | 100 | 93 | 78 |

Parsol 1789 has chemical formula:

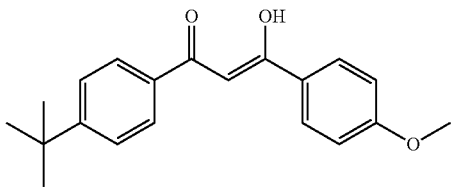 [SMILES: COc1ccc(/C(O)=C/C(=O)c2ccc(C(C)(C)C)cc2)cc1]

Parsol MCX has chemical formula:

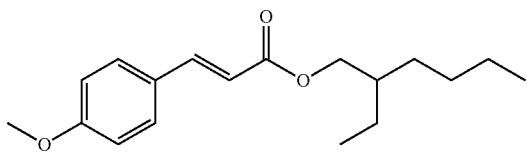 [SMILES: CCCCC(CC)COC(=O)/C=C/c1ccc(OC)cc1]

Octocrylene has chemical formula:

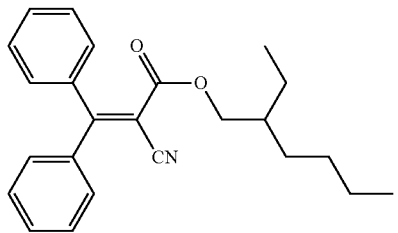 [SMILES: CCCCC(CC)COC(=O)C(C#N)=C(c1ccccc1)c1ccccc1]

Compound of present invention has the chemical formula:

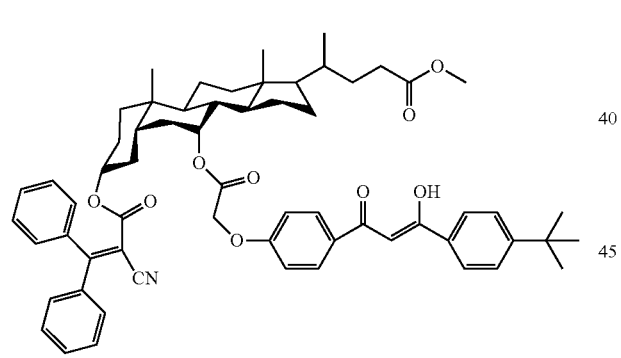

The above compound was prepared using the following method

Stage 1: Esterification of Chenodeoxycholic Acid

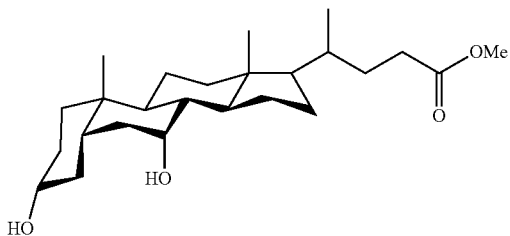

Synthesis of Methyl Ester of Chenodeoxy Cholic Acid (10 g, 0.0254 moles) of chenodeoxycholic acid was taken in a two necked round bottom flask fitted with air condenser; under the inert atmosphere of nitrogen. 100 mL of methanol was added as the solvent. The catalytic amount of concentrate sulfuric acid was added to methanol-chenodeoxycholic acid solution. The reaction mixture was stirred at 25° C. for 24 h. The progress of the reaction was monitored by via TLC using hexane-ethyl acetate (90:10) as the mobile phase. The reaction mixture was concentrated and dissolved in chloroform. The organic mixture was washed with sodium bicarbonate solution until the pH of aqueous wash was neutral. The organic layer was further washed with water. It was separated out and dried under anhydrous sodium sulfate. Methyl ester of chenodeoxycholic acid was isolated by distilling off chloroform. The crude product was further purified using column chromatography, using hexane-ethyl acetate (100:0 to 80:20) and 230-400 mesh size silica to obtain white yellow powder with 70% yield. FT-IR analysis (KBr/cm$^{-1}$) of compound showed peaks at 3300 cm$^{-1}$ (broad peak) due to —OH; 1730 cm$^{-1}$ due to C—O stretching in carbonyl group. $^1$HNMR (CDCl$_3$) peaks at δ ppm 3.9 (s, $^1$H, HO—CH(CH$_2$)$_2$ at C-7), 3.65 (s, 3H, COOCH$_3$), 3.45 (m, 1H, HO—CH(CH$_2$)$_2$ at C-3), 0.7 (s, 3H C-18 or C19); 0.9 (s, 6H C-18 or C19 & C21). $^{13}$CNMR (CDCl$_3$) δ ppm peaks at 174 (s, C(O)OCH$_3$, C-24), 71.97 (HO—CH(CH$_2$)$_2$ at C7), 68.49 (HO—CH(CH$_2$)$_2$ at C3), 55.76 & 50.43 (C17, C-14); 51.46 (C(O)OCH$_3$ at C-25).

Stage 2: Synthesis of 2-cyano-3,3-diphenylacrylic acid

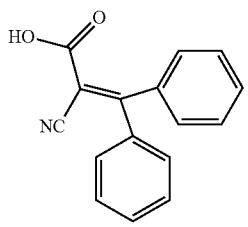 [SMILES: N#CC(C(=O)O)=C(c1ccccc1)c1ccccc1]

Synthesis of 2-cyano-3,3-diphenylpropenoic acid 2-ethylhexyl 2-cyano-3,3-diphenyl-2-propenoate (25 g, 0.07 moles) was dissolved in 50 mL Ethanol. 16 g (0.4 moles) of Sodium hydroxide (95%) was dissolved in 65 mL water in 250 mL double necked round bottom flask. The solution of 2-ethylhexyl 2-cyano-3,3-diphenyl-2-propenoate was then added drop-wise to sodium hydroxide solution. After stirring for nearly 24 h at room temperature the reaction mixture was extracted twice with 50 mL Ethyl acetate to remove unreacted 2-ethylhexyl 2-cyano-3,3-diphenyl-2-propenoate. The aqueous layer was acidified with 1N HCl and resulting pale yellow solid was dried. The compound showed IR spectrum peaks (KBr/cm$^{-1}$) at 3063 cm$^{-1}$ due to C—H in aromatic ring; 2222 cm$^{-1}$ due to C—N strerchings; 1689 cm$^{-1}$ due to C—O stretching in Carbonyl group; stretching in 1594 cm$^{-1}$ due to C=C stretching in aromatic rings; Molecular ion peak was observed at 248.9; Product absorbs UV at 291 nm and 226 nm ($\lambda_{max}$) at 10 ppm concentration $^1$H NMR δ (CDCl3) peaks at 7.15-7.55 (10 H, complex, Ar—H); $^{13}$C NMR δ H (CDCl3) peaks at 116.978 (CN), 128.243, 128.532, 129.564, 130.418, 130.738, 131.759, 138.265, 138.435, 166.310 (COOH).

Stage 3: Covalent Attachment of 2-cyano-3,3-diphenylacrylic acid-UVB (at C-3 Position) to Methyl ester of chenodeoxycholic acid

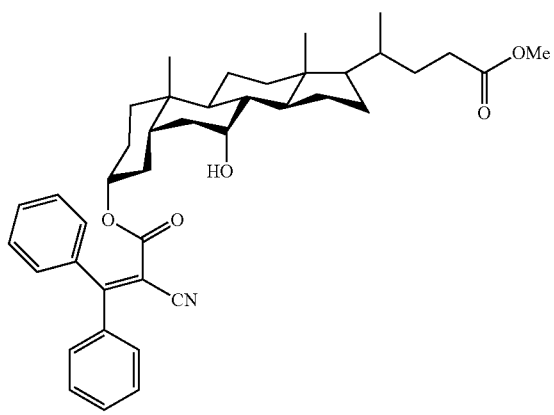

UVB Modified methyl ester of Chenodeoxy Cholic acid (3α,7α-dihydroxy-5β-cholanic acid)

2-cyano-3,3-diphenylacrylic acid (3.1 g, 0.0124 moles), dicyclohexylcarbodiimide (DCC, 2.8 g, 0.014 moles) and N,N-dimethylamino pyridine (DMAP, 0.15 g, 0.0012 moles) were taken in a two necked round bottom flask containing 30 mL of dichloromethane (DCM) under the inert atmosphere of nitrogen. The reaction mixture was stirred at 25° C. for 2 h. Methyl ester of chenodeoxycholic acid (5 g, 0.0123 moles) was dissolved in 50 mL of DCM was added to the reaction mixture. The reaction mixture was further stirred at 25° C. for 5 h. The progress of the reaction was monitored by using TLC using Chloroform as the mobile phase. The reaction mixture was filtered off to remove dicyclohexylurea. The DCM filtrate was washed with dilute HCl to remove DMAP. The crude product was further purified using column chromatography, using hexane: ethylacetate (100:0 to 80:20) and 230-400 mesh size silica·mwt of product-637.38 as the white crystalline solid with 40% yield. Molecular ion peak was observed at 660.4 (M+23 (Na). Product absorbs UV at 301 nm and 222 nm ($\lambda_{max}$) at 10 ppm concentration. δH (CDCl$_3$) peaks at 7-7.5 (complex, 10H, Ar—H); 4.55 (m, 1H, —C(O)O—CHCH$_2$ at C3), 3.9 (broad s, 1H, HO—CHCH$_2$ at C7), 3.65 (s, 3H, COOCH$_3$), 0.7 (s, 3H C18 or C19); 0.9 (s, 6H C18 or C19 & C21). $^{13}$C NMR δ$_C$ (60 MHz, CDCl$_3$) peaks at 174 (C(O)OCH3, C24), 116.978 (CN), 128.243, 128.532, 129.564, 130.418, 130.738, 131.759, 138.265, 138.435, 166.310 71.97 (HO—CH(CH2)2 at C7), 55.76 & 50.43 (C17, C14); 51.46 (C(O)OCH3 at C25).

Stage 4: Derivatization of UVB Attached Methyl Ester of Chenodeoxycholic Acid at C-7 Position

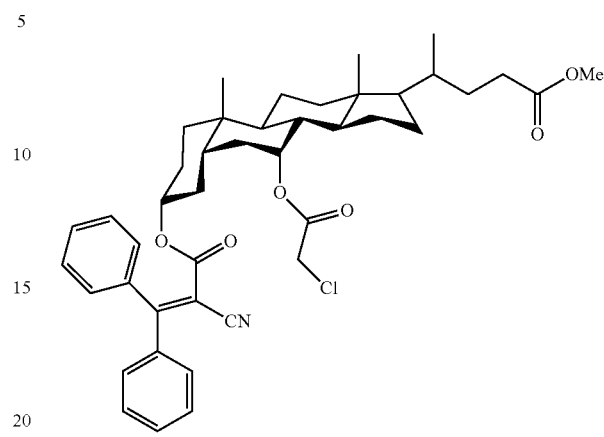

Synthesis of UVB & Linker Modified Methyl Ester of Chenodeoxy Cholic Acid (IUPAC)

UVB modified methyl ester of chenodeoxy cholic acid (100 mg, 1.57×10$^{-4}$ moles), chloro acetyl chloride (85.2 mg, 7.5×10$^{-4}$ moles), calcium hydride (6.5 mg, 1.57×10$^{-4}$ moles) and tetramethylammonium iodide 3.1 mg (1.57×10$^{-5}$ moles) were taken in a two necked round bottom flask under the inert atmosphere of nitrogen. 20 mL of HPLC grade toluene was added as the solvent. The reaction mixture was refluxed for 20-24 h. The progress of the reaction was monitored by TLC using chloroform as the mobile phase. After completion of the reaction, the organic reaction mixture was washed with brine solution (300 mL) until pH of the aqueous layer was neutral. The organic layer was dried with anhydrous sodium sulfate. The dried organic layer was further concentrated to give white crystalline powder with 60% yield. Molecular ion peak was observed at 736.5 (M+23 (Na). Product showed UV absorption at $\lambda_{max}$ 310 nm at 10 ppm concentration. $^1$HNMR δH (CDCl$_3$) peaks at 7-7.5 (m, 10H, aromatic region); 4.9 (broad s, 1H, —C(O)O—CHCH2 at C$_7$), 4.55 (m, 1H, —C(O)O—CHCH$_2$ at C$_3$); 3.65 (s, 3H, COOCH$_3$), 0.7 (s, 3H C$_{18}$ or C$_{19}$); 0.9 (s, 6H C$_{18}$ or C$_{19}$ & C$_{21}$).

Stage 5: Synthesis of 4-tert-butyl-4'-hydroxy dibenzoylmethane

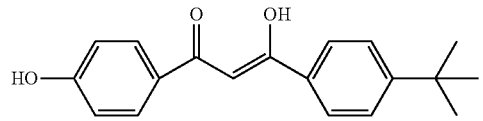

Synthesis of 4-hydroxy, 4'-tert-butyl dibenzoylmethane

A 1000 mL of 3-necked, round bottom flask fitted with dropping funnel, and reflux condenser is charged with sodium hydride 60% oil dispersion (12 g, 0.40 moles) which is washed twice with hexane. Next 200 mL of dry glyme is added and the slurry heated to reflux with stirring A solution of 4-hydroxyacetophenone (13.62 g, 0.10 mol) dissolved in 100 mL if glyme is added dropwise. The reaction mixture is allowed to reflux for 45 minutes after the addition. Next, a solution of methyl-4-tert-butyl benzoate (17.79 g, 0.10 moles) dissolved in 100 mL of glyme is added dropwise. The reaction mixture is allowed to reflux for 16 hours, after which time most of the of the glyme was distilled off. The pot residue is cooled in an ice bath and 300 mL of ether is added followed by the cautious addition of 200 mL of water. The aqueous layer was separated. The ether layers washed with cold water (2×200 mL). The combined aqueous layers carefully poured onto a Mixture of 400 g of ice plus 90 mL of concentrated HCl. The yellowish green solid that precipitates is collected by suction filtration and washed with little cold water. This crude product is purified by column chromatography by using (hexane to 50% Ethyl acetate in hexane) as the yellow crystalline solid with 50% yield. Molecular ion peak was observed at 293.8. Product absorbs UV at 358 nm ($\lambda_{max}$) at 10 ppm concentration; $\delta_H$ (300 MHz, CDCl$_3$) peaks at 1.34 (s, 9H, —C(CH$_3$)$_3$), 6.78 (s, 1H, C(O)—CH=C(OH)), 6.92 (2H, 3'& 5'-aromatic proton), 7.48 (2H, 3& 5-aromatic proton) 7.88 (2H, d, 2 & 6-aromatic protic), 16.85 (1H, s-broad, —OH(enol); $\delta_C$ (300 MHz, CDCl$_3$) peaks at 31.0, 35.06, 49.85, 92.23, 115.66, 125.66, 125.85, 128.95, 129.59, 132.47, 156.17, 160.11, 184.40, 186.22.

Stage 6: Covalent Attachment of
4-tert-butyl-4'-hydroxy dibenzoylmethane at C-7
Derivatized Methyl ester of chenodeoxycholic acid

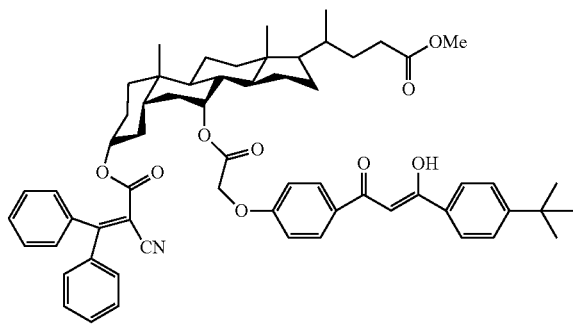

Synthesis of UVB & UVA modified methyl ester of chenodeoxy cholic acid 4-hydroxy, 4'-tert-butyl dibenzoylmethane (44.4 mg, 1.501×10$^{-4}$ moles), potassium carbonate (0.1 g, 7.2×10$^{-4}$ moles) were taken in a two necked round bottom flask under the inert atmosphere of nitrogen. 20 mL of dry acetone was added subsequently. The reaction mixture was refluxed for 2 h. After 2 h of reflux, UVB & Linker modified methyl ester of chenodeoxy cholic acid (IUPAC) (107.1 mg, 1.501×10$^{-4}$ moles), sodium iodide (2.25 mg, 1.501×10$^{-5}$ moles) were added. Reaction mass was further reflux and progress of the reaction was monitored by TLC using Chloroform as the mobile phase. The reaction mass was filtered to remove insoluble potassium carbonate. Acetone was distilled off from the filtered reaction mass and chloroform was added. The organic reaction mixture was washed with 3×100 mL of brine solution until pH of the aqueous layer was neutral. The organic layer was dried with anhydrous sodium sulfate and concentrated to give UVB & UVA modified methyl ester of chenodeoxy cholic acid. Appearance of the product is white crystalline powder with yield of around 50%. Molecular ion peak was observed at 997 (M+23 (Na). Product absorbs UV at 357 nm and 290 nm ($\lambda_{max}$) at 10 ppm concentration. $^1$HNMR $\delta$H (CDCl$_3$) peaks at 3.9 (m, 1H, HO—CH(CH$_2$)$_2$ at C$_7$), 3.65 (s, 3H, COO CH$_3$), 3.45 (m, 1H, HO—CH(CH$_2$)$_2$ at C$_3$), 0.7 (s, 3H C$_{18}$ or C$_{19}$); 0.9 (s, 6H C$_{18}$ or C$_{19}$ & C$_{21}$), 4.0 (m, 2H, C$_7$—OCO CH$_2$Cl) 1.34 (9H, s, C(CH$_3$)$_3$) 6.78 (1H, s2-H), 6.92 (2H, d, Ar—H (3-H, 5-H) 7.48 (2H, d, Ar—H (3'-H, 5'-H), 7.88 (2H, d Ar—H (2-H, 6-H), 16.85 (1H, s (broad), OH).

The data in Table 1 indicates that the sunscreen molecule as per the invention (Example 5) and a composition comprising the inventive molecule along with a UVB sunscreen (Example 6) exhibit high stability.

Example 7 & 8: Stability of the Sunscreen Active of the Invention in a Sunscreen Formulation In this example, the stability of a sunscreen formulation comprising the molecule of the present invention (Example 7) is compared to the stability of a sunscreen formulation comprising the sunscreen actives individually (Example 8) at 0, 60 and 120 minutes.

TABLE 2

| Ingredients | Example 7 | Example 8 |
|---|---|---|
| Molecule of present invention | 4.8 | 0 |
| Avobenzone |  | 1.5 |
| Ethylhexyl methoxycinnamate | 6 | 6 |
| Octocrylene |  | 1.7 |
| Abil em 90 | 1 | 1 |
| Caprylic/Capric Triglycerides | 20 | 20 |
| KCl | 2 | 2 |
| Water | 66.2 | 67.8 |
| Total | 100 | 100 |

Stability was measured by the following procedure:

The above compositions were applied on glass slides (2 mg/cm$^2$) and were exposed to simulated sunlight from an artificial sunlamp (SUNTEST™CPS, from Heraeus) for 0, 60 and 120 minutes respectively. After exposure for the indicated time in minutes, the contents on the glass slides were dissolved using methanol in 25 ml standard flasks, where the volumes were fixed to 25 ml. UV absorption curves were plotted using (PERKIN ELMER UV/Visible Spectrometer) for each test samples using deionised methanol as reference. Absorption values (A) were recorded at 355 nm for each of sample. The percentage of Absorbance values (which is an indicator of the degree of photo-degradation of the UVA chromophore) were calculated using following formula:

$$\% A = \frac{(\text{Absorbance at } \lambda_{max} \text{ per unit weight})}{(\text{Absorbance at } \lambda_{max} \text{ per unit weight at time} = 0)} \times 100$$

The results are tabulated below:

TABLE 3

| Time in minutes | UVA stability of Example 7 | UVA stability of Example 8 |
|---|---|---|
| 0 | 100 | 100 |
| 60 | 95.40929204 | 63.31351 |
| 120 | 86.28318584 | 30.03333 |

The data in Table 3 indicates that the sunscreen formulation comprising the molecule of the present invention (Example 7) exhibits a higher stability at 60 and 120 minutes than the formulation comprising the sunscreen actives individually (Example 8).

The invention claimed is:

1. A broad spectrum sunscreen molecule having the structure

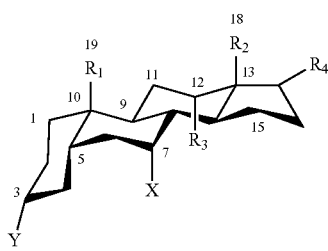

where,

R1 and R2 are selected from C1 to C20 linear or branched alkyl, C3-C10 cycloalkyl, polycycloalkyl, heterocyclic, aryl, alkoxy, alkenyl or alkynyl groups, R3 is —H or —OH or R1, R4 is selected from C1 to C20 linear or branched alkyl, C3-C10 cycloalkyl, polycycloalkyl, heterocyclic, aryl, alkoxy, alkenyl or alkynyl groups containing carboxylic acid group in free form or its esterderivative; or R4 is H or is selected from C1 to C20 linear or branched alkyl, C3-C10 cycloalkyl, polycycloalkyl, heterocyclic, aryl, alkoxy, alkenyl or alkynyl groups containing carboxylic acid;

wherein the acid group is attached to the polymer through ester linkage; or

R4 is the same as R1 or R2; or

R4 is an organoheteryl group or a polymer backbone or cross-polymer backbone or rigid organic or inorganic support covalently attached through the hetero atom, "X" is an organic sunscreen belonging to the UVA class and "Y" is an organic sunscreen belonging to UVB class, or vice-versa.

2. The sunscreen molecule of claim 1 wherein R1, R2, R3 are each a methyl group and R4 is 4-pentanoic acid methyl ester.

3. The sunscreen molecule of claim 1 wherein said organic UVA sunscreen, X, is a dibenzoyl methane, a benzophenone, or a triazine compound.

4. The sunscreen molecule of claim 1 wherein said UVB organic sunscreen, Y, is selected from the class of cinnamate, salicylate, diphenyl acrylate derivatives, triazine, triazole, and imidazole compounds.

5. The sunscreen molecule of claim 1 wherein X is a dibenzoyl methane compound and Y is a dipenyl acrylate compound.

6. The sunscreen molecule of claim 5 having the structure

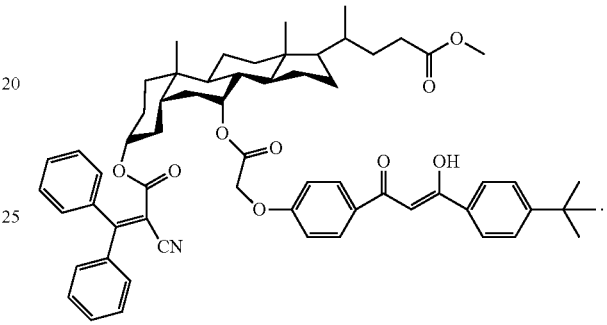

7. A stable sunscreen composition comprising
(i) a sunscreen molecule as claimed in claim 1;
(ii) a UV-B organic sunscreen belonging to the class of cinnamate, salicylate, diphenyl acrylate derivatives, triazine, triazole, and imidazole compounds, and
(iii) a cosmetically acceptable base.

8. A method of providing UV protection to the sun-exposed parts of a human or animal body comprising the step of applying the composition as claimed in claim 7 on to the desired part.

* * * * *